United States Patent [19]

Swedo

[11] Patent Number: 5,206,383

[45] Date of Patent: Apr. 27, 1993

[54] O,O'-BISMALEIMIDE RESIN SYSTEMS

[75] Inventor: Raymond J. Swedo, Mt. Prospect, Ill.

[73] Assignee: Allied-Signal Inc., Morris Township, Morris County, N.J.

[21] Appl. No.: 827,182

[22] Filed: Jan. 28, 1992

[51] Int. Cl.[5] .................. C07D 207/452; C07F 7/02
[52] U.S. Cl. ..................................... 548/521; 548/406
[58] Field of Search ............................. 548/406, 521

[56] References Cited

U.S. PATENT DOCUMENTS

| | | | |
|---|---|---|---|
| 3,562,223 | 2/1971 | Bargain et al. | 260/78 |
| 4,100,140 | 7/1978 | Zahir et al. | 526/90 |
| 4,116,937 | 9/1978 | Jones et al. | 528/170 |
| 4,239,880 | 12/1980 | Darms | 528/125 |
| 4,460,783 | 7/1984 | Nishikawa et al. | 548/549 |
| 4,464,520 | 8/1984 | Adams et al. | 526/262 |
| 4,808,646 | 2/1989 | Dahms | 524/104 |
| 4,816,512 | 3/1989 | Dahms | 524/606 |
| 4,855,450 | 8/1989 | Butler et al. | 548/522 |
| 4,904,801 | 2/1990 | Butler et al. | 548/521 |
| 4,970,292 | 11/1990 | Bockrath et al. | 528/353 |

FOREIGN PATENT DOCUMENTS

| | | | |
|---|---|---|---|
| 0382198A2 | 2/1990 | European Pat. Off. | 548/521 |
| 0388657A1 | 2/1990 | European Pat. Off. | 548/521 |
| 0413087A1 | 4/1990 | European Pat. Off. | 548/406 |
| 0425265A1 | 10/1990 | European Pat. Off. | 548/521 |

OTHER PUBLICATIONS

Mikroyannidis et al., *British Polymer Journal*, 23, 309 (1990).
Bell et al., *Journal of Polymer Science*, Polymer Chemistry Edition, 14, 2275 (1976).
Ghatge et al., *Polymer*, 22, 1250 (1981).
Bell et al., *Journal of Polymer Science: Part A: Polymer Chemistry* vol. 24 "Isomeric Bismaleimides and Polyaspartimides", pp. 2647–2655 (1986).

CA 116(2): 7575 p Heat-resistant polyamide-imide adhesive compositions Hirai et al., 1992.

*Primary Examiner*—Mary C. Lee
*Assistant Examiner*—Joseph K. McKane
*Attorney, Agent, or Firm*—Mary Jo Boldingh; Harold N. Wells; Gerhard H. Fuchs

[57] ABSTRACT

This invention concerns novel o,o'-bismaleimide resins which have good processibility, novel o,o'-diamines used to prepare the resins, and the novel o,o'-bismaleimide polymers prepared by curing these resins. The polymers have thermo-oxidative and tensile properties which rival conventional p,p'- and m,m'-bismaleimide resin systems.

The o,o'-bismaleimide resins of this invention have the following structure:

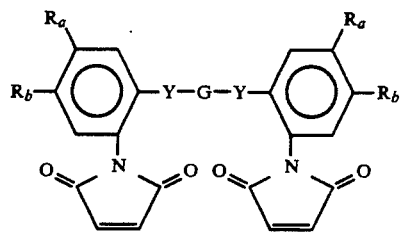

wherein Y—G—Y is a bridging group with Y selected from the group consisting of oxygen, sulfur, and selenium, and G selected from a number of structures having aromatic and/or siloxane character. $R_a$ and $R_b$ are independently selected from the group consisting of hydrogen, an alkyl containing up to 4 carbon atoms, the corresponding alkoxy groups, chlorine, and bromine, or $R_a$ and $R_b$ together form a fused 6-membered aromatic ring.

4 Claims, No Drawings

O,O'-BISMALEIMIDE RESIN SYSTEMS

BACKGROUND OF THE INVENTION (1) Field of the Invention

This invention relates generally to bismaleimide resins with good processability, to the polymers made from the resins which have thermal stability and toughness, and to the production of such resins Application areas include composites, laminates, printed wiring boards, and pultrusion and resin transfer molding for the aerospace, automotive, and electronics industries.

(2) Description of the Related Art

Aromatic bismaleimides are widely used thermosetting resins having properties especially suitable for high temperature, high performance applications where they are employed as matrix resins and binders for composite molded components and laminates.

Typically, bismaleimide resin systems possess desirable thermo-oxidative and tensile properties, but poor processing properties. The poor processing properties of the resins occur because they begin to polymerize at temperatures which are at or only slightly above their melting points, making it very difficult to obtain homogeneous resin melts prior to resin gelation. This inhomogeneity is especially deleterious in the fabrication of composites or large molded parts because, upon heating, the outer portions of these fabricated pieces reach the curing temperature of the resin before the center portions of the pieces are completely melted and if the mixture is inhomogeneous, cracks and other defects are generated when final molding pressures are applied, e.g., due to high concentrations of trapped gases.

Conventional bismaleimide systems use R bridging groups such as $CH_2$, O, S, $SO_2$, and $C(CH_3)_2$. Recently, various structural modifications in the aromatic bismaleimides have been attempted in order to improve the processibility of the resins while maintaining the desirable end use properties such as thermo-oxidative stability, mechanical strength, and solvent resistance possessed by the conventional systems. Modifications have been made to the general aromatic bismaleimide structure (I):

$$\text{Im—Ar—R—Ar—Im} \quad (I)$$

where Ar is generally a phenyl or substituted phenyl ring, Im a maleimide group, and R a bridging group between the two Ar groups, by changing the structure of R, the structure of Ar, and the configuration of the attachment of R and Im to the two Ar groups.

Adams et al. ("Adams"), in U.S. Pat. Nos. 4,464,520 and 4,564,683, produced a resin with aliphatic R bridging groups $S—(CH_2)_n—S$, $O—(CH_2)_n—O$, and $Se—(CH_2)_n—Se$ (n=1-3) attached in an o,o'-configuration. However, unlike previously synthesized o,o'-resins, this resin had a "broad processing window," i.e., a broad temperature range in degrees centigrade between the peak melting temperature and the onset of polymerization as observed by differential scanning calorimetry (DSC) analysis.

SUMMARY OF THE INVENTION

This invention concerns novel o,o'-bismaleimide resins which have good processability, novel o,o'-diamines used to prepare the resins, and the novel o,o'-bismaleimide polymers prepared by curing these resins. The polymers have thermo-oxidative and tensile properties which rival conventional p,p'- and m,m'-bismaleimide resin systems.

The o,o'-bismaleimide resins of this invention have the following structure (II):

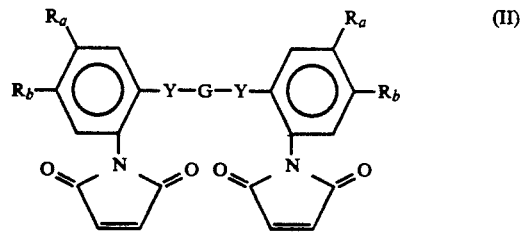

wherein the Y—G—Y group replaces the R group of structure (I). Curing these resins results in superior polymeric bismaleimides.

This invention also concerns o,o'-aromatic diamines which are the precursors to the novel resins. These diamines have the following structure (III):

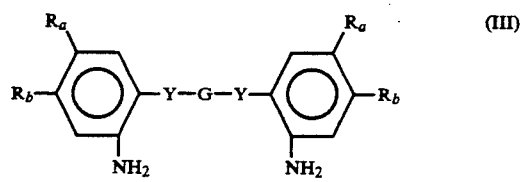

In both structures above, the bridging group is Y—G—Y, and Y is selected from the group consisting of oxygen, sulfur, and selenium. $R_a$ and $R_b$ are independently selected from the group consisting of hydrogen, an alkyl containing up to 4 carbon atoms (methyl, ethyl, propyl, isopropyl, n-butyl, sec-butyl, iso-butyl), the corresponding alkoxy groups (methoxy, ethoxy, propoxy, isopropoxy, n-butoxy, iso-butoxy), chlorine, and bromine, or $R_a$ and $R_b$ together form a fused 6-membered ring, e.g., the maleimido and Y groups can be attached to a naphthyl ring instead of a phenyl ring. $R_a$ and $R_b$ are preferably both hydrogen. Preferred alkyl and alkoxy groups for $R_a$ and $R_b$ are those having one or two carbon atoms. The halo-containing compounds are desirable because of the resultant smoke and fire retardancy which is imparted to the corresponding resins.

G is selected from the group consisting of:

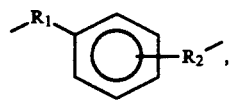

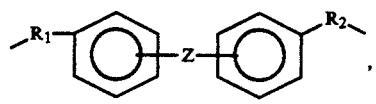

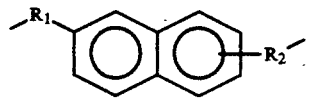

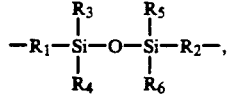

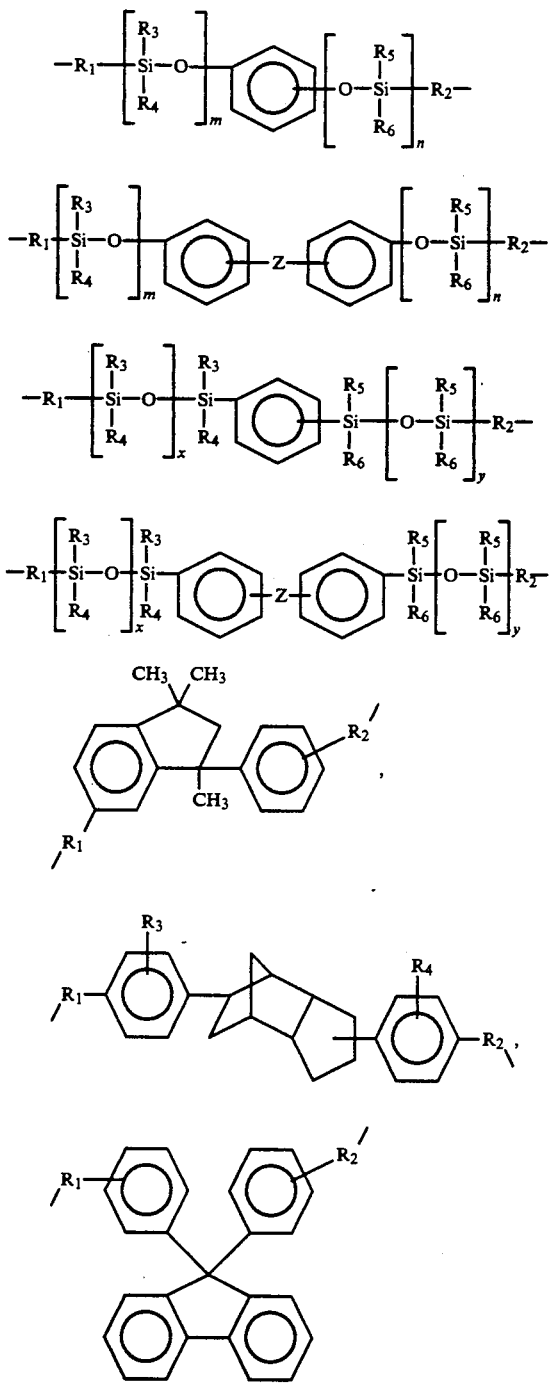

where Z is a covalent single bond, or is selected from the group consisting of O, S, SO$_2$, C=O, CH$_2$, C(CH$_3$)$_2$, C(CF$_3$)$_2$, and [Si(CH$_3$)$_2$O]$_n$; R$_1$ and R$_2$ are single bonds or CH$_2$; R$_3$, R$_4$, R$_5$, and R$_6$ are alkyl groups containing from 1 to 6 carbons or are phenyl groups; m and n are integers from 1 to 10; x and y are integers from 0 to 10.

The G bridging groups are made up of essentially two components: aromatic groups and/or siloxanes. Siloxanes have stronger bonds than aliphatic groups and could be expected to lend good thermal stability and greater flexibility to the bismaleimide. The aromatic rings add good thermal stability and increased strength and stiffness properties. The combination of siloxane and aromatic groups could be expected to produce a bismaleimide with a greater melting point and a greater glass transition temperature than a simple siloxane but it was not known until now that the steric hindrance to synthesizing this bismaleimide could be overcome. The silicone-containing bismaleimides, especially where m, n, x, y >1, should lower the melting temperature and broaden the processing window.

Finally, this invention concerns a process for preparing an o,o'-bismaleimide resin comprising reacting the o,o'-aromatic diamine with maleic anhydride in a dipolar aprotic solvent at a temperature of 40° to 60° C., as well as a polymeric o,o'-bismaleimide having good thermo-oxidative and tensile properties, prepared by the process comprising the steps of: preparing the o,o'-bismaleimide resin, heating said resin to a temperature greater than or equal to its melting point and less than the temperature at which it begins to polymerize, holding said heated resin at a temperature less than the temperature at which it begins to polymerize for a period of time sufficient to obtain a homogeneous melt, degassing said heated resin, further heating said degassed resin to the temperature at which it polymerizes and polymerizing said resin; and slowly cooling said polymerized resin to recover said polymeric bismaleimide.

It is the object of this invention to provide o,o'-bismaleimide resins which have good processing properties as well as good end product properties and to provide resins can be polymerized and shaped in the form of molded articles.

DESCRIPTION OF THE PREFERRED EMBODIMENTS

The object of this invention is met by providing novel o,o'-bismaleimide resins (structure II above), novel polymers prepared by curing these resins, and novel o,o'-aromatic diamine precursors (structure III above) from which the resins may be synthesized.

As discussed above, Adams produced a resin with aliphatic R bridging groups S—(CH$_2$)$_n$—S, O—(CH$_2$)$_n$—O, and Se—(CH$_2$)$_n$—Se (n=1-3) attached in an o,o'-configuration with a broad processing window. However, the aliphatic nature of Adams' S—CH$_2$—CH$_2$—S bridging group provided cured resin systems which had thermo-oxidative and strength properties inferior to those of the more conventional aromatic diamine-based p,p'-systems. The resins of the instant invention provide o,o'-bismaleimide resins with a broad processing window comparable to Adams' system along with cured resin properties comparable to the conventional systems.

The novel o,o'-aromatic diamine precursors can be prepared using conventional methods. Two different approaches are summarized schematically below. A typical approach begins with the synthesis of a bis-o-nitro ether following a nucleophilic aromatic substitution process utilizing excess potassium carbonate in NMP (N-methyl-pyrrolidinone) and toluene or in DMAC (N,N'-dimethylacetamide) and toluene at about 150° to about 190° C. for 6 to 12 hours. The nitro groups are then catalytically hydrogenated to the o,o'-aromatic diamine precursors using typical conditions and catalysts An alternative approach is the direct synthesis of the o,o'-aromatic diamine precursor by the reaction of o-aminophenols or o-aminothiophenols with dihalides using a four-fold excess of powdered potassium hydroxide/dimethylsulfoxide slurry. The reactions are typically conducted at temperatures of from about 0° C. to about 70° C., and are usually complete in from about 30 to about 60 minutes.

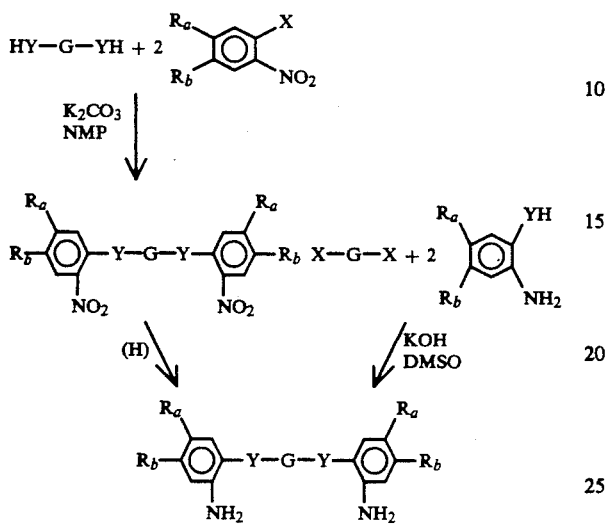

Other approaches to preparing the precursors may be found in basic organic chemistry texts. Regardless of the synthetic approach, it is important that the bridging groups ("R" in structure (I)) be attached to the aromatic groups ("Ar" in structure (I)) by an o,o'-configuration.

The novel o,o'-bismaleimide resins disclosed in this invention (II) can be prepared from the novel o,o'-aromatic diamine precursors using conventional methods. One such process involves the reaction of the diamine with a 10 mole % excess of maleic anhydride in acetone solvent at room temperature to generate a bis-maleamic acid. A suspension of the bis-maleamic acid is then treated with excess acetic anhydride and catalytic sodium acetate in refluxing acetone for 2 to 3 hours to generate the bismaleimide. Another approach is to conduct the cyclodehydration of the maleamic acid to the maleimide using a catalytic amount of sodium acetate in excess acetic anhydride as the solvent at a reaction temperature of 90° C. for about one hour.

Our preferred method for the conversion of the novel o,o'-aromatic diamine precursors to the novel o,o'-bismaleimides involves reacting the diamines with preferably slightly more than a stoichiometric amount of maleic anhydride in a dipolar aprotic solvent such as dimethylformamide (DMF), N-methyl-pyrrolidinone (NMP), dimethylsulfoxide (DMSO), at temperatures of from about 40°–60° C., preferably 50°–60° C., and typically about 55° C. After reacting for about two hours, the solution of bis-maleamic acid is cooled, then an excess of acetic anhydride and a catalytic amount of anhydrous sodium acetate are added, and the mixture is further reacted for two hours at 55°–60° C., and more preferably at 58° C., to produce the o,o'-bismaleimide. The preferred process is shown schematically below.

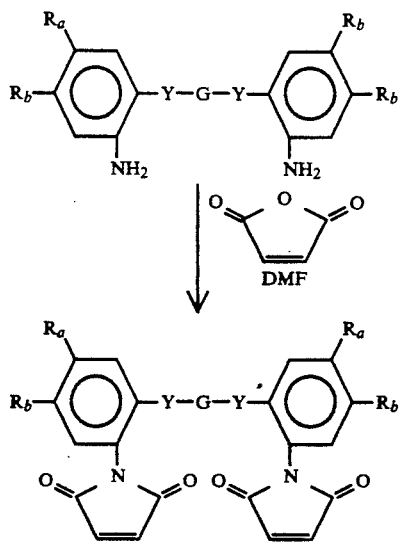

The bismaleimide resins thus obtained are useful in the preparation of laminated or molded objects either by using the neat resins alone or by using the bismaleimides as matrix resins or binders. To these ends, the bismaleimide resins are melted by heating at temperatures greater than or equal to their melting points, and less than the temperatures at which they begin to polymerize, until a homogeneous melt is obtained. The melted samples may then be degassed under vacuum for a period in the range of from about 15 to 30 minutes or until the samples are no longer actively outgassing. After the vacuum is released, the samples are cured typically at a temperature in the range of from about 175° C. to about 180° C. for a period in the range of from about 2 to about 12 hours, then at a temperature in the range of from about 200° C. to about 210° C. for a period in the range of from about one to about 8 hours, and finally at a temperature in the range of from about 240° to about 260° C. for a period in the range of from about 4 to about 8 hours. The cured samples are allowed to cool slowly to avoid stress cracking. Specific polymerization conditions can be optimized using fully conventional considerations and routine parametric experiments where necessary.

The key features of the novel bismaleimides disclosed in this invention are the sterically hindered o,o'-configuration by which the bridging groups are attached to the aromatic groups and the choice of the bridging group itself. The following examples illustrate the beneficial properties obtained by these key features and, in particular, the importance of the choice of bridging group in obtaining these properties.

EXAMPLE 1

Synthesis of Novel Diamines. The novel bismaleimide resins were prepared from novel diamines as follows:

A 500 mL 3-neck flask was fitted with a mechanical stirrer, a reflux condenser, a thermometer, and a $N_2$ bubbler. The flask was charged with 21.2 g (85 wt. %, 0.32 mole) of finely ground KOH, and 500 mL of dimethylsulfoxide (DMSO). The slurry was stirred vigorously under $N_2$, and 0.16 mole of either o-aminophenol or o-aminothiophenol was added. The slurry darkened and warmed to a temperature in the range of from about 40° to about 65° C. When the mixture had cooled to about 40° C., a solution of 0.07 moles of o-, m-, or p-xylene (depending upon the bridging group "G" desired) in 50 mL of DMSO was added. An exotherm to a temperature of about 50° to 70° C. occurred and the mixture became lighter in color. After stirring vigorously under $N_2$ for 1.5 hours, the reaction mixture was poured into 750 mL of water.

The mixture was extracted with 3×100 mL of methylene chloride or diethylether The combined extracts were washed with 1×250 mL of water and with 1×250 mL of saturated aqueous NaCl. The methylene chloride or diethylether solution was then dried over anhydrous $CaCl_2$ and the solvent was removed by rotary evaporation. The resins prepared from these amines will be labeled EOX, EMX, EPX, TOX, TMX, and TPX, wherein "E" signifies that the resin contains ether connections between the aromatic groups and the bridging group and "T" signifies that there are thioether connections "OX," "MX," and "PX" signify that the bridging group in the resin is ortho-, meta-, or para-xylyl, respectively The amines corresponding to the EOX, EMX, and TMX resins were light brown mobile liquids; the TOX, EPX, and TPX amines were solids Amine yields were EOX 91%, TOX 90%, EMX 94%, TMX 98%, EPX 38% (problems with experiment), TPX 89%.

Analyses of the Diamines. The structures of the diamines were confirmed by elemental microanalysis, infrared spectroscopy and nuclear magnetic resonance spectroscopy.

EXAMPLE 2

Synthesis of Novel Bismaleimides. The bismaleimides were prepared as follows using the novel diamines of Example 1. A 1 L resin kettle was fitted with a mechanical stirrer, a reflux condenser, a $N_2$ bubbler, a thermometer, and a heating mantle with temperature controller. The kettle was charged with 38.44 g (0.392 moles) of maleic anhydride and 300 mL of dimethylformamide (DMF) (vacuum distilled from $P_2O_5$ drying agent). The mixture was stirred under $N_2$ until a clear, colorless solution was obtained To this solution 0.178 mole of a diamine prepared in Example 1 were added followed by an additional 200 mL of DMF. A mild exotherm (to 30° to 40° C.) was noted.

The mixture was heated to about 40° C., and was maintained at about 40°-45° C. for 1 hour. The temperature of the mixture was then increased to 50° C. and was maintained at 50°-55° C. for 2.5 hours. The reaction mixture was cooled to 45° C. and 0.047 mole anhydrous sodium acetate and 0.44 mole acetic anhydride were added. The reaction mixture was heated to 55°-60° C. and was maintained at this temperature for 3.5 hours.

The mixture was then poured into 2 L of 2 wt % aqueous NaCl solution and a solid product precipitated. The product was collected by filtration and washed on the filter with a total of 5 L deionized water. The product was dried in air for several hours, then dried under vacuum at 40 C overnight Resin yields were EOX 95%, TOX 100%, EMX 77%, TMX 70%, EPX 100%, TPX 100%.

The resins prepared have o-, m-, and p-xylyl groups as the bridging groups ("G") and ether and thioether as connecting groups ("Y"). The diamines with the desired bridging groups and connecting groups were used to prepare each resin The resins are labeled EOX, EMX, EPX, TOX, TMX, and TPX, wherein "E" signifies that the resin contains ether connections between the aromatic groups and the bridging group and "T" signifies that there are thioether connections "OX," "MX," and "PX" signify that the bridging group in the resin is ortho-, meta-, or para-xylyl, respectively.

Synthesis of the Standard Bismaleimide. The standard bismaleimide was prepared in the same manner as were the novel bismaleimides, but using 1,2-bis-(2-aminophenylthio)ethane to provide a $CH_2CH_2$ bridging group and a sulfur connecting group between the bridging group and the aromatic group.

Analyses of the Bismaleimides. The structures of the bismaleimides were verified by elemental microanalysis, infrared spectroscopy and nuclear magnetic resonance spectroscopy.

EXAMPLE 3

The novel and standard bismaleimide resins prepared in Example 2 were cured by heating the neat resin under a $N_2$ purge in a vacuum oven until a homogeneous melt was obtained. The melted samples were then degassed under vacuum for 15 to 30 minutes. After the vacuum was released, the samples were cured under $N_2$ at 175° to 180° C. for 2 to 12 hours, then at 200° to 210° C. for one to 8 hours, and finally at 240° to 260° C. for 4 to 8 hours. The cured samples were allowed to cool slowly under $N_2$ to avoid stress cracking.

EXAMPLE 4

The properties of the diamines and the cured and uncured bismaleimides prepared in Examples 1 and 2 were measured by a number of methods.

Thermal properties. The thermal properties were tested by differential scanning calorimetry (DSC), thermal gravimetric analysis (TGA), isothermal aging (ITA), and by determining the glass transition temperature ($T_g$).

DSC was conducted under $N_2$ at $\Delta T=5°$ C./min for the uncured resins to determine the processing window and $\Delta T=10°$ C./min for the cured resins to determine the $T_g$. Results showed that only three of the new bismaleimides, TMX, TOX, and EMX showed reasonable processing windows ($T_{poly}$ onset minus $T_{melt}$ peak; see Table 1).

These results, however, are unexpected. The conventional bismaleimide has a bridging group with a p,p'-configuration as well as a p,p' attachment between the aromatic rings and the bridging groups and good thermal and mechanical properties. The Standard bismaleimide presented here has a $CH_2CH_2$ bridging group and an o,o' attachment and has good processibility. If the benefits provided by these two types of bismaleimide were additive, one might expect that a bismaleimide with a p,p' bridging group and an o,o' attachment would provide a bismaleimide with both benefits.

However, the data in Table 1 show that the properties are not additive. The combination of the p,p' bridging group and an o,o' attachment, Resins TPX and EPX, produced resins with very narrow processing windows typical of conventional aromatic diamine-based bismaleimide resins. When m,m' bridging groups were substituted, Resins TMX and EMX, the processing windows were found to be unexpectedly wider than even the Standard o,o'-bismaleimide. When o,o' bridging groups were used, the resin with the sulfur connecting group, Resin TOX, had a processing window comparable to the standard o,o'-bismaleimide, while the resin with an oxygen connecting group, Resin EOX, had a narrower processing window, but one still wider than the windows of the conventional aromatic diamine-based bismaleimide resins.

TABLE 1

| Resin | T$_{melt}$ onset °C. | T$_{melt}$ peak °C. | T$_{poly}$ onset °C. | T$_{poly}$ peak °C. | Processing Window °C. |
|---|---|---|---|---|---|
| Standard | 109 | 147 | 222 | 287 | 75 |
| TPX | 49 | 200 | 200 | 235 | 0 |
| TMX | 58 | 90 | 220 | 278 | 130 |
| TOX | 50 | 120 | 185 | 245 | 65 |
| EPX | 60 | 224 | 225 | 247 | 1 |
| EMX | 48 | 63 | 176 | 213 | 113 |
| EOX | 60 | 187 | 204 | 252 | 17 |

The T$_g$ values were determined by DSC and appear in Table 2. The values for the new xylylether bridged resins (EOX, EMX, EPX) were lower than the values observed for the standard, while the values for the xylylthioether bridged resins (TOX, TMX, TPX) were desirably equal to or higher than those of the standard.

TGA was conducted in air at $\Delta T=10°$ C./min. Data appear in Table 2. Results showed that the novel bismaleimide resins had lower 5 wt. % loss temperatures than the standard bismaleimide. But, TGA is a dynamic measurement and does not predict long-term use of a resin at a given temperature. Therefore, ITA was performed on cured neat resin samples. The data appear in Table 2. The samples were first dried under vacuum at 100° C. for 24 hours and allowed to cool to room temperature in a desiccator. The samples were weighed, then placed in an air circulating oven maintained at 204° C. Weight loss was monitored by periodically removing the samples, cooling them in a desiccator, and reweighing them before returning them to the oven. ITA indicates the thermal-oxidative stability of a material. Results showed that after 2,000 hours at 204° C. in air EMX, TOX, TMX, and TPX all had better thermal stabilities (lower losses) than the standard resin.

TABLE 2

| Resin | DSC T$_g$, °C. | TGA, °C. Loss in Air 5 wt. % | ITA % Wt. Loss |
|---|---|---|---|
| Standard | 300 | 385 | 8.5 |
| EPX | 275 | 365 | 26.8 |
| TPX | 370 | 437 | 2.2 |
| EMX | 292 | 320 | 5.9 |
| TMX | 300 | 369 | 0.9 |
| EOX | 275 | 363 | 14.1 |
| TOX | 351 | 358 | 1.5 |

EXAMPLE 5

Solvent Resistance. The solvent resistance of the bismaleimide resins prepared in Example 2 was determined by measuring the water and CH$_2$Cl$_2$ uptake of each dried cured resin. The resins were weighed before and after being suspended in an excess of distilled water and maintained at reflux for 24 hours and before and after being suspended in an excess of CH$_2$Cl$_2$ maintained at room temperature for 72 hours. Resins TOX and TMX were superior to the standard in that they had lower water uptake values. Resins EMX and TMX were superior to the standard in CH$_2$Cl$_2$ uptake values.

TABLE 3

| Resin | Wt. % H$_2$O Uptake | Wt. % CH$_2$Cl$_2$ Uptake |
|---|---|---|
| Standard | 2.51 | 5.04 |

TABLE 3-continued

| Resin | Wt. % H$_2$O Uptake | Wt. % CH$_2$Cl$_2$ Uptake |
|---|---|---|
| EPX | 26.6 | 21.9 |
| TPX | — | — |
| EMX | 10.8 | 1.7 |
| TMX | 2.0 | 2.7 |
| EOX | 56.1 | 29.7 |
| TOX | 2.47 | 7.47 |

EXAMPLE 6

Tensile properties. Overall, the new o,o'-bismaleimide with the best properties was the TMX resin. Tensile specimens of this resin were prepared by making the resin formulation in a beaker, curing the resin by heating it to melting in N$_2$, then degassing the resin under vacuum until it became quiescent, usually about 30 minutes. The vacuum was then replaced by N$_2$ and the degassed melts were then poured into silicon rubber tensile specimen molds. The melted resins in the molds were again vacuum degassed until the melts became quiescent. The vacuum was again replaced by N$_2$ and the specimen was cured in the mold at 175° C. for 24 hours. The specimens were then carefully removed from the molds and further cured at 240° C. for 24 hours under N$_2$. The fully cured specimens were then cooled to room temperature slowly to avoid stress cracking.

The TMX tensile test specimen was then evaluated according to ASTM D638-86, TMX was found to have higher strength, strain, and modulus values than the Standard formulation. See Table 4.

TABLE 4

| Resin | Strength MPa | (kpsi) | Strain % | Modulus MPa | (kpsi) |
|---|---|---|---|---|---|
| Standard | 16.89 | (2.45) | 0.39 | 4350.59 | (631) |
| TMX | 47.09 | (6.83) | 1.11 | 4433.33 | (643) |

I claim:

1. An o,o'-bismaleimide resin with good processibility having the formula:

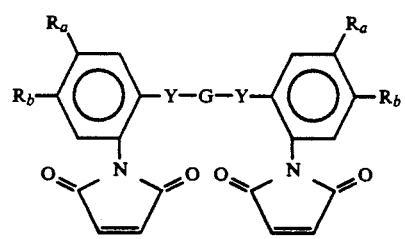

wherein Y is selected from the group consisting of oxygen, sulfur, and selenium, R$_a$ and R$_b$ are selected from the group consisting of hydrogen, methyl, ethyl, propyl, isopropyl, n-butyl, sec-butyl, iso-butyl, methoxy, ethoxy, propoxy, isopropoxy, n-butoxy, iso-butoxy, chlorine, and bromine, or R$_a$ and R$_b$ together form a fused 6-membered carbocyclic ring, G is selected from the group consisting of:

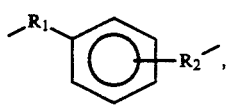

-continued

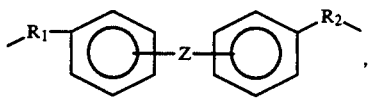

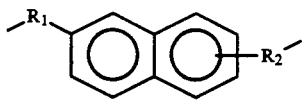

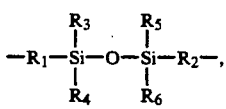

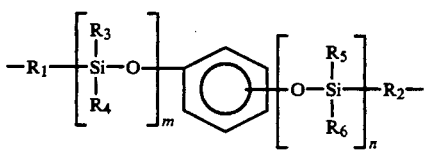

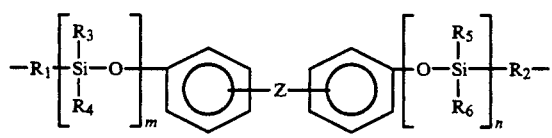

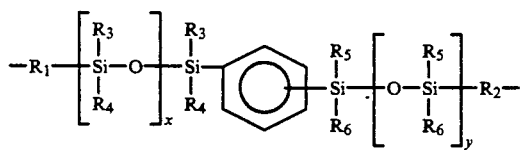

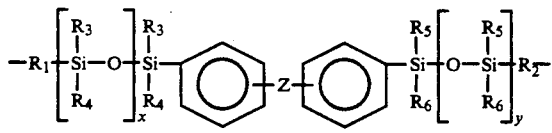

-continued

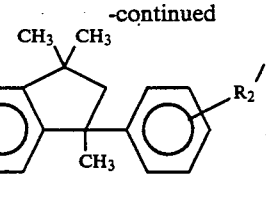

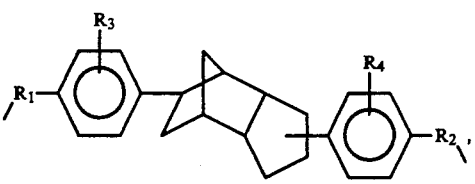

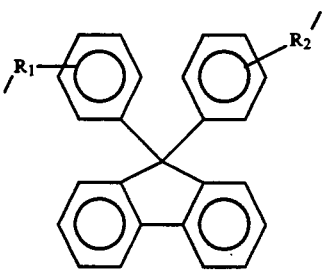

where Z is a covalent single bond, or is selected from the group consisting of O, S, $SO_2$, C=O, $CH_2$, $C(CH_3)_2$, $C(CF_3)_2$, and; $R_1$ and $R_2$ are $CH_2$; $R_3$, $R_4$, $R_5$, and $R_6$ are alkyl groups containing from 1 to 6 carbons or are phenyl groups; m and n are integers from 1 to 10; and x and y are integers from 0 to 10.

2. The o,o'-bismaleimide resin of claim 1 wherein Y is selected from the group consisting of oxygen, sulfur, and selenium, $R_a$ and $R_b$ are hydrogen, and G is selected from the group consisting of o-, m-, and p-xylyl.

3. The o,o'-bismaleimide resin of claim 2 wherein Y is sulfur and G is m-xylyl.

4. The o,o'-bismaleimide resin of claim 2 wherein Y is oxygen and G is m-xylyl.

* * * * *